(12) United States Patent
Sonkusale et al.

(10) Patent No.: US 11,484,262 B2
(45) Date of Patent: Nov. 1, 2022

(54) THREAD-BASED INTEGRATED FUNCTIONAL DEVICES

(71) Applicant: Trustees of Tufts College, Medford, MA (US)

(72) Inventors: Sameer Sonkusale, Arlington, MA (US); Pooria Mostafalu, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 518 days.

(21) Appl. No.: 15/749,207

(22) PCT Filed: Jul. 29, 2016

(86) PCT No.: PCT/US2016/044639
§ 371 (c)(1),
(2) Date: Jan. 31, 2018

(87) PCT Pub. No.: WO2017/023727
PCT Pub. Date: Feb. 9, 2017

(65) Prior Publication Data
US 2018/0228436 A1 Aug. 16, 2018

Related U.S. Application Data

(60) Provisional application No. 62/199,638, filed on Jul. 31, 2015.

(51) Int. Cl.
| | | |
|---|---|---|
| A61B 5/1455 | (2006.01) | |
| A61B 5/00 | (2006.01) | |
| A61B 5/01 | (2006.01) | |
| A61B 5/145 | (2006.01) | |
| G01N 27/12 | (2006.01) | |
| G01N 27/403 | (2006.01) | |

(Continued)

(52) U.S. Cl.
CPC .............. *A61B 5/6804* (2013.01); *A61B 5/00* (2013.01); *A61B 5/01* (2013.01); *A61B 5/14503* (2013.01); *A61B 5/14532* (2013.01); *A61B 5/681* (2013.01); *A61B 5/6851* (2013.01); *G01N 27/127* (2013.01); *G01N 27/403* (2013.01); *A61B 5/14539* (2013.01); *A61B 2560/0443* (2013.01); *B82Y 15/00* (2013.01); *B82Y 30/00* (2013.01)

(58) Field of Classification Search
CPC ..... A61B 5/1455; A61B 5/01; A61B 5/14503; A61B 5/14532
See application file for complete search history.

(56) References Cited

U.S. PATENT DOCUMENTS

| | | |
|---|---|---|
| 4,600,310 A | 7/1986 | Cramp et al. |
| 6,264,612 B1 | 7/2001 | McConnell et al. |

(Continued)

FOREIGN PATENT DOCUMENTS

| | | |
|---|---|---|
| CN | 104501840 | 4/2015 |
| WO | 2012038522 | 3/2012 |

*Primary Examiner* — Marjan Fardanesh
(74) *Attorney, Agent, or Firm* — Occhiuti & Rohlicek LLP

(57) ABSTRACT

A composite thread includes first and second segments joined to each other. The first segment comprises a functional segment that interacts with an environment of the thread. The second segment communicates information between the first segment and a point external to said composite thread.

18 Claims, 2 Drawing Sheets

(51) Int. Cl.
    *B82Y 15/00*         (2011.01)
    *B82Y 30/00*         (2011.01)

(56) References Cited

U.S. PATENT DOCUMENTS

2012/0153262 A1\* 6/2012 Paranjape ............. H01L 51/055
                                                      257/24
2013/0041235 A1   2/2013 Rogers et al.
2015/0366504 A1\* 12/2015 Connor ................ A61B 5/0492
                                                      600/301

\* cited by examiner

THREAD-BASED INTEGRATED FUNCTIONAL DEVICES

CROSS REFERENCE TO RELATED APPLICATIONS

This application is a National Phase under 35 USC 371 of International Application No. PCT/US2016/044639 filed on Jul. 29, 2016, which claims priority to U.S. Provisional Application No. 62/199,638 filed Jul. 31, 2015, the contents of which are hereby incorporated by reference in their entirety.

FIELD OF INVENTION

This invention pertains to device integration, and in particular, to integration of devices that can be worn or implanted.

BACKGROUND

As a result of advances in miniaturization and device integration, it is now possible to have wearable sensors that provide data about the wearer more or less continuously or on demand. These sensors can be worn outside the body, in which case they are often called "smart wearable systems." They can also be worn inside the body, in which case they are often called "implantable diagnostic devices."

The devices themselves are typically integrated into a two-dimensional manifold. In some cases, the manifold is a rigid planar structure, in which case devices cannot move relative to each other. However, in many cases, the devices are integrated into a flexible two-dimensional manifold. Smart clothing, in which devices are disposed on a flexible fabric, provides an example of this.

SUMMARY

The invention generally provides smart wearable systems and implantable diagnostic devices in which various components are integrated into a one-dimensional manifold. This is advantageous because a one-dimensional manifold can be moved more easily through a three-dimensional space.

The invention achieves this by integrating various components onto a thread, thus forming a composite thread that carries out multiple functions. As used herein, "thread" includes flexible, essentially one-dimensional structures such as filament, fiber, yarn, floss, including dental floss, string, line, and twine. What these structures have in common is that they are essentially one-dimensional and flexible.

Threads have traditionally been used in the apparel industry. The invention exploits the flexibility of threads to permit fabrication of composite threads having functional features and I/O features in the same thread. The wicking property of such threads permits their use as microfluidic channels within such a composite thread.

As a result of its flexibility and one-dimensionality, composite thread as described herein can be interfaced intimately with biological tissues in three dimensions to implement a thread-based diagnostic platform. Functional features include physical and chemical sensors to monitor physiochemical properties of tissues and fluids in the vicinity of the composite thread.

In some embodiments, physical and chemical sensors are fabricated from nanomaterial infused threads connected to a wireless electronic read-out using thread-based flexible interconnects for signal conditioning and wireless transmission. Exemplary sensors are those used to measure mechanical properties, such as strain, and chemical properties, such as gastric and subcutaneous pH.

In one aspect, the invention features a composite thread having first and second segments joined to each other. The first segment includes a functional segment that interacts with an environment of the thread, and the second segment communicates information between the first segment and a point external to the composite thread.

In some embodiments, the first segment includes a sensor. Among these embodiments are those in which the sensor senses a physical property and those in which it senses a chemical property.

Embodiments in which the sensor senses a physical property include those in which it senses strain and those in which it senses temperature. In these embodiments, the sensor can be a strain sensor or a temperature sensor. Embodiments in which the sensor senses a chemical property include those in which it senses pH and those in which it senses glucose.

In some embodiments, the first segment has an elastic thread. A suitable material for elastic thread in at least some embodiments is polyurethane. Among the embodiments that have an elastic thread are those in which the elastic thread is coated with an inner layer and an outer layer. The inner layer can be a carbon nanotube layer or a carbon nanoparticle layer. The outer layer can be a polydimethylsiloxane layer. Also among these embodiments are those in which the second coating is selected to protect the first coating from delamination during stretching and relaxation of the elastic thread.

In yet other embodiments, the first segment includes a thread having electrical properties that vary with strain applied to the thread.

In other embodiments, the first segment includes a thread coated with any one or more of nickel, platinum, and carbon nanotubes.

Further embodiments include those in which the first segment is a biomarker, those in which it is a glucose sensor, and those in which it is an amperometric glucose sensor.

In some embodiments, the first segment includes first, second, and third electrodes. The first electrode includes thread coated with functionalized carbon nanotubes, the carbon nanotubes having been functionalized by addition of carboxyl groups, wherein the second electrode includes thread coated with carbon nanoparticles, and wherein the third electrode includes a reference electrode.

In some embodiments, the first segment includes a first thread section coated with polyalanine.

In another embodiment, the first segment includes a first thread section coated with a material having a property that varies with pH.

Embodiments also include those in which the second segment is electrically conducting and those in which it is not.

In some embodiments, the second segment includes a thread having a coating of conductive material, such as silver, carbon nanotubes, and/or silver chloride.

The segments can be joined together in any of a variety of ways. These include knotting, braiding, gluing, or twisting the segments together.

Further embodiments include those in which there is a third segment. The third segment is joined to either one of the first and second segments and forms a microfluidic flow channel. These embodiments include those in which the third segment includes a hydrophilic thread, either with or without a hydrophobic coating along a section thereof. Also included among these embodiments are those in which the third segment includes hydrophilic thread that has been treated by oxygen plasma, those in which the third segment includes hydrophilic thread having a surface to which hydroxyl groups have been added, and those in which the third segment includes hydrophilic thread having a silicone lubricant coating at least along a section thereof Also among the embodiments are those that have a third segment, a fourth segment, and a fifth segment, all of which are microfluidic channel segments. In these embodiments, the three segments join together at a common point.

In some embodiments, the first segment includes a payload to be delivered to surrounding tissue. Among these embodiments are those in which the second segment includes a channel for carrying a signal that controls delivery of the payload. The channel can be a conductive channel or one that functions as a waveguide. An example of the latter is a dielectric that is transparent to electromagnetic waves having wavelengths in the visible range.

In another aspect, the invention features a functional component that interacts with the living body, and a communication component that carries information indicative of the interaction, with the functional component and the communication component being integrated into a thread.

In yet another aspect, the invention features an integrated circuit that has components integrated into a substrate, the substrate being a flexible thread.

BRIEF DESCRIPTION OF THE FIGURES

These and other features of the invention will be apparent from the following detailed description and its accompanying figures, in which.

DETAILED DESCRIPTION

Figure 1:
FIG. 1 shows a composite thread.

FIG. 1 shows a composite thread 10 formed by joining an I/O segment 12 and a functional segment 14 at a first junction 16.

In some embodiments, the functional segment 14 is a sensor that generates a signal indicative of an extent of some physical property. Examples of such sensors include those that sense some manifestation of thermal energy and those that sense some manifestation of mechanical energy. Examples of the former include temperature sensors. Examples of the latter include strain sensors.

In other embodiments, the functional segment 14 is a sensor that senses a chemical property. Examples of such sensors include pH sensors, and sensors that generate a signal indicative of the presence and/or concentration of a chemical, such as glucose or other biomarkers.

In either case, the signal must be communicated to someone or something or it will not be very useful. The I/O segment 12 carries out this function.

The nature of the I/O segment 12 depends on the nature of the signal generated by the segment thread 14. For those cases in which the signal is a voltage or current, the I/O segment 12 is a conductive thread. For those cases where the signal is an electromagnetic wave, the I/O segment 12 is a waveguide for guiding that wave. As an example, where the electromagnetic wave has a wavelength in the visible range, the I/O segment 12 can be an optical fiber.

The functional segment 14 can also be used to deliver a payload. For example, the functional segment 14 can be soaked in an ionic solution. In that case, the I/O segment 12 can deliver a voltage that will control flow of the ions into fluid surrounding the functional segment 14. A functional element 14 of this type can thus be used for release of drugs. In some cases, the functional element 14 may be divided into different zones, each of which has a particular drug with its own ionic formulation. In that case, application of a particular voltage could trigger release of some but not all drugs. This provides a way to control release of different drugs using the same thread.

Figure 2:
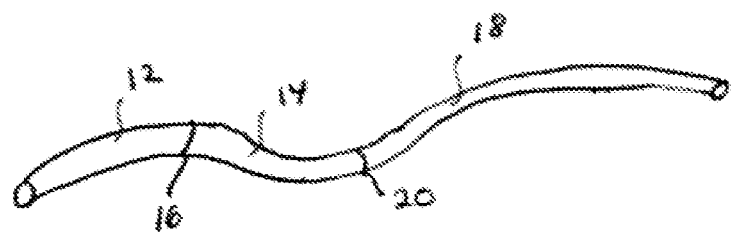
FIG. 2 shows the composite thread of FIG. 1 with the addition of a fluid channel.

In some cases, it is useful to provide fluid communication between the functional segment 14 and a target site. To achieve this, a microfluidic segment 18 is joined to the functional segment 14 at a second junction 20, as shown in FIG. 2.

To make the various segments described above, one dips thread into one or more solutions, the nature of which will depend on the type of segment to be made. In principle, it is possible to use one continuous thread and to dip different segments into different solutions. However, it is more practical to manufacture a type of segment by the spool and to simply cut and join segments as necessary. The junctions 16, 20 between these segments can be formed by twisting threads together, by braiding them together, by gluing them together, or by otherwise attaching them. In the particular embodiment shown in FIG. 3, the two segments are knotted together.

Figure 4:
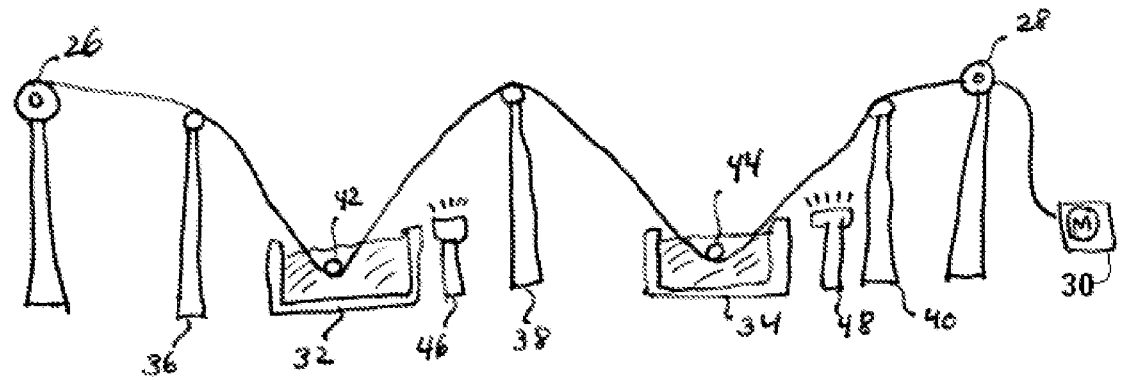
FIG. 4 shows an apparatus for manufacturing one of the segments of the composite thread shown in FIGS. 1 and 2.

FIG. 4 illustrates a manufacturing apparatus 22 for making a segment 24 that will ultimately be joined to other segments to form a composite thread. The manufacturing apparatus 22 features a first spool 26 around which is wound a raw thread and a second spool 28 that takes up finished thread. A motor 30 causes the second spool 28 to rotate, thus drawing thread from the first spool 26 and causing it to traverse a processing path.

As shown, the processing path includes first and second baths 32, 34, first, second, and third dry spindles 36, 38, 40, which are outside the baths 32, 34, first and second wet spindles 42, 44, which are in the respective first and second baths 32, 34, and first and second drier stations 46, 48 disposed just downstream of the first and second baths 32, 34 respectively.

In operation, the motor 30 rotates the second spool 28, thus causing a tensile force to pull on thread in the first spool 26. This causes each infinitesimal thread element to traverse a path that takes it around the first dry spindle 36 and into the first bath 32, around the first wet spindle 42 and out of the first bath 32 the first drying station 46, around the second dry spindle 38 and into the second bath 34, around the second wet spindle 44, past the second drying station 48, up to the third dry spindle 40, until it finally reaches the second spool 28.

At each bath 32, 34, a solution containing a desired material is added to the thread. The aqueous portion of the solution is then evaporated at each dryer 46, 48 so that only the desired material is left behind. The number of baths depends on the number of materials to be added. FIG. 4 shows two baths for the sake of example. It is understood that there can be only one bath and that there can be more than two baths.

In some embodiments, an I/O segment 12 is made by passing cotton thread through a bath 32 that includes a conductive ink. Examples of conductive ink include solutions of silver, silver chloride, carbon, carbon nanotubes, graphene, reduced graphene oxide, zinc oxide, metallic nanowires, semiconducting nanowires, nanopowders and nanoparticles of dielectric, metallic and semiconducting types, and polyanaline. This results in the incorporation of material within the thread. To the extent the incorporated material is conductive, the resulting I/O segment 12 is electrically conductive, and is thus suitable to function as an electrode. On the other hand, if the incorporated material is non-conductive, such as dielectric, insulating, or semiconducting nanopowders, nanoparticles or nanorods, the I/O segment 12 will function as a semiconducting or insulating wire.

The conductive ink can include a color dye to enable the I/O segment 12 to be seen more clearly. In some methods, a dryer cures the coating. Illumination with an ultra violet source can be used as needed to sterilize the I/O segment 12.

In some embodiments, the functional segment 14 is made by passing an elastic thread through one or more baths to infuse carbon nanotubes or carbon nanoparticles and a protective coating of polydimethylsiloxane.

The use of polydimethylsiloxane is particularly useful to protect the conductive layer from scratching, to enhance mechanical integrity of the thread, and to avoid delamination as the elastic thread stretches and relaxes.

A suitable material from which to make the elastic thread is polyurethane. Polyurethane is a thermoplastic that can be chemically activated when plasma-treated. Conductive threads made with polyurethane have greater conductivity than other elastic threads.

A thread along the lines of the foregoing acquires different electrical characteristics, such as resistance, as a function of its deformation. As such, it forms the basis of a strain sensor. When connected to an I/O segment 12 formed as an electrode, the resulting composite thread can be used to obtain signals indicative of strain.

It is also possible to use carbon ink, or an ink made with other conducting or semiconducting nanoparticles, nanopowders and nanowires instead of carbon nanotubes. However, strain sensors made with carbon nanotubes can measure higher strains. This is believed to be the result of carbon nanotubes having higher deformability than carbon nanoparticles as a result of their fibrous stricture. In addition, the use of carbon nanotubes offers the advantage of faster response time and lower creep.

Another advantage of using carbon nanotubes is that there is a naturally strong adhesion between the carbon nanotubes and the polyurethane thread. A coating on a polyurethane thread will, in general, tend to buckle and fracture as a result of the constant stretching and relaxation. The adhesion between the carbon nanotubes and the polyurethane is such that this tendency is suppressed. This tends to preserve the linear behavior of the elastic thread and avoids undermining its elasticity.

A suitable application for a composite thread having a strain sensor is to monitor the healing of an incision, particularly when the incision is not easily accessible. It is known that as tissue heals, it changes shape. A thread sutured into that area, or embroidered on a woven construct sutured to the area, would thus experience changes in tension. A composite thread that has a strain sensor could be used to monitor healing. For example, if no change in strain is detected for an extended period, it would indicate that the wound is not healing rapidly and suggest the desirability of some intervention.

Another method of making a functional segment 14 includes joining a first section with nano-infused thread coated with carbon and polyanaline with a second section coated with silver or silver chloride. This method makes use of the way polyanaline changes state depending on whether it is in an acidic or basic environment. The first section and second sections thus form a working electrode and a reference electrode of a pH meter.

A composite thread that measures pH is advantageous because pH affects so many biochemical processes. For example, pH of a wound correlates with angiogenesis, protease activity, and bacterial infection. Healing proceeds more readily at low pH, however an excessively low pH may indicate bacterial infection. Gastric pH measurements are likewise essential to diagnosis of gastrointestinal diseases, such as inflammatory bowel, gastro-esophageal reflux diseases, and infections from *helicobacter pylori*.

Polyanaline has numerous other advantages in this application. It is biocompatible, it has high electrical conductivity and it is remarkable stable in the presence of electrolytes. Additionally, polyanaline offers some mechanical advantages. For instance, polyanaline forms a thin layer with a three-dimensional network of interconnected nanofibrils. This layer promotes mechanical flexibility and enhances the mechanical integrity of the coated layer.

Coating the thread with nickel or platinum can make another functional segment 14. These metals are particularly useful because their resistance changes with temperature more or less linearly over ranges of biological interest. Additionally, carbon nanotubes can be used to coat the thread. The resulting functional segment 14 thus operates as a temperature sensor.

A composite thread having a temperature sensor is particularly useful because temperature variation is an indicator of inflammation or bacterial infection. Additionally, since many biochemical processes are temperature dependent, knowledge of temperature is useful in connection with many other assays of amounts of various chemicals.

Yet another functional segment 14 can be made by joining three pieces of thread that form corresponding first, second, and third electrodes. The first electrode is made by coating thread with carbon functionalized carbon nanotubes. Functionalized carbon nanotubes can be made by adding carboxylic groups and binding the result to plasma-treated threads. The second electrode is made from thread coated with carbon nanoparticles. The third electrode is made from conductive thread, such as thread that has been coated with, or otherwise infused with silver or silver chloride. In this embodiment, the resulting functional segment 14 is an amperometric glucose sensor that can be used to measure glucose concentration in the presence of glucose oxidase enzyme solution immobilized by nafion.

Figure 3:
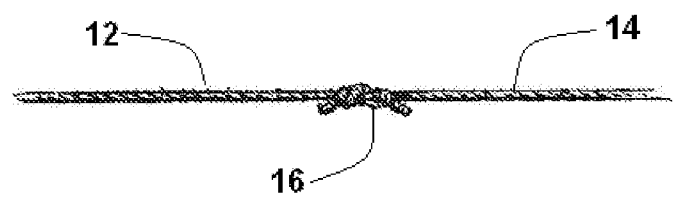
FIG. 3 shows one of several ways to join two segments together to form the composite threads shown in FIGS. 1 and 2.

In the embodiment shown in FIG. 3, the microfluidic segment 18 can be formed by first treating cotton thread with oxygen plasma. This is desirable because commercially available cotton thread is coated with a wax, which reduces its ability to wick aqueous solutions. The oxygen plasma not only removes the wax but adds hydroxyl groups to the thread surface, thus making it particularly hydrophilic.

In some cases, the microfluidic segment 18 may have to transport fluid across a region without losing fluid or absorbing more fluid. In that case, the thread can be coated with a hydrophobic substance along an appropriate length thereof. A suitable hydrophobic substance is commercially available silicone lubricant.

Figure 5:
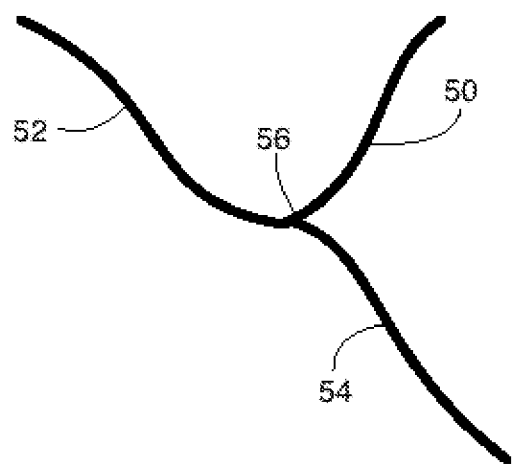
FIG. 5 shows a three-way junction made from microfluidic segments of the type shown in FIG. 2.

In other cases, it may be desirable to cause flow on one channel to be divided between two channels, or conversely, for flow in two channels to be combined into one channel. This can be achieved, as shown in FIG. 5, by first, second, and third microfluidic channels 50, 52, 54 at a common junction 56.

The techniques described herein, and the devices made according to those techniques create an ability to measure physical and chemical markers in the body in vivo. The physical markers explicitly described are strain, and temperature, The chemical markers explicitly described are pH, and glucose. However the subject matter disclosed herein can be applied to other measurements in vivo.

The devices described herein are made from threads of the type that are already used in the apparel industry. The threads can be tailored for transporting fluids using capillary action. Or, they can be infused with nanomaterials for performing electrochemical sensing by simply dipping the threads in appropriate media.

Thread-based systems as described herein can be used on the human skin, in clothing, or implanted. The ability to suture such thread-based diagnostic devices intimately with a tissue or organ that extends in three dimensions adds a unique feature that is not available with other flexible diagnostic platforms.

Thread-based diagnostic systems as described herein can be used as smart sutures for surgical implants, and as smart bandages to monitor wound healing. In addition, they can be integrated with textile or fabric, where they can function as personalized health monitors or sources of point of care diagnostic information. Such thread-based diagnostic systems can also be embedded into tissue-engineered constructs for organs.

Other markers can be detected, such as markers for measuring proteins, and nucleic acids directly in the tissue in which the system has been implanted. Such markers can be detected by functionalizing the threads based on the appropriate chemistry.

Having described the invention, and a preferred embodiment thereof, what is claimed as new, and secured by Letters Patent is:

1. An apparatus comprising a composite thread having a first Segment including a first terminating end and a second segment including a second terminating end, wherein said first and second terminating ends are joined to each other, wherein said first segment comprises a functional segment that interacts with an environment of said thread, and wherein said second segment communicates information between said first segment and a point external to said composite thread.

2. The apparatus of claim 1, further comprising a third segment, wherein said third segment is joined to one of said first and second segments and wherein said third segment comprises a microfluidic flow channel.

3. The apparatus of claim 2, wherein said second segment comprises a thread that comprises carbon nanotubes.

4. The apparatus of claim 2, wherein said first and second segments are knotted together.

5. The apparatus of claim 2, wherein said first segment comprises an elastic thread, a first coating, and a second coating, wherein said first coating coats said elastic thread, wherein said second coating coats said first coating, wherein said first coating comprises carbon nanotubes, and wherein said second coating comprises polydimethylsiloxane.

6. The apparatus of claim 2, wherein said first segment comprises an elastic thread, a first coating, and a second coating, wherein said first coating coats said elastic thread and said second coating coats said first coating, wherein said first coating comprises carbon nanoparticles, and wherein said second coating comprises polydimethylsiloxane.

7. The apparatus of claim 2, wherein said first segment comprises elastic thread, a first coating, and a second coating, wherein said second coating is selected to protect said first coating from delamination during stretching and relaxation of said elastic thread.

8. The apparatus of claim 2, wherein said first segment comprises a thread having electrical properties that vary with strain applied to said thread.

9. The apparatus of claim 2, wherein said first segment comprises a biomarker sensor.

10. The apparatus of claim 2, wherein said first segment comprises first, second, and third electrodes, wherein said first electrode comprises thread coated with functionalized carbon nanotubes, said carbon nanotubes having been functionalized by addition of carboxyl groups, wherein said second electrode comprises thread coated with carbon nanoparticles, and wherein said third electrode comprises a reference electrode.

11. The apparatus of claim 2, wherein said third segment comprises hydrophilic thread.

12. The apparatus of claim 2, wherein said third segment comprises hydrophilic thread having a hydrophobic coating at least along a section thereof.

13. The apparatus of claim 2, wherein said third segment comprises hydrophilic thread that has been treated by oxygen plasma.

14. The apparatus of claim 2, wherein said third segment comprises hydrophilic thread having a surface to which hydroxyl groups have been added.

15. The apparatus of claim 2, wherein said third segment comprises hydrophilic thread having a silicone lubricant coating at least along a section thereof.

16. The apparatus of claim 2, further comprising a fourth segment and a fifth segment, wherein said fourth segment and said fifth segment are microfluidic channel segments, wherein said fourth segment is joined to said third segment at a point, and wherein said fifth segment is joined to both said fourth segment and said third segment at said point.

17. The apparatus of claim 2, wherein said first segment comprises a payload to be delivered to surrounding tissue and wherein said second segment comprises a channel for carrying a signal that controls delivery of said payload.

18. The apparatus of claim 2, wherein said apparatus consists of components that are integrated into a one-dimensional manifold, where said components are said first, second, and third segments.

* * * * *